United States Patent
Harttig et al.

(10) Patent No.: US 7,879,291 B2
(45) Date of Patent: Feb. 1, 2011

(54) MANUAL DEVICE FOR EXAMINING A BODY FLUID

(75) Inventors: Herbert Harttig, Neustadt (DE); Hans List, Hesseneck-Kailbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/814,890

(22) Filed: Jun. 14, 2010

(65) Prior Publication Data

US 2010/0249567 A1 Sep. 30, 2010

Related U.S. Application Data

(60) Division of application No. 11/405,275, filed on Apr. 17, 2006, now Pat. No. 7,758,808, which is a continuation of application No. PCT/EP2004/011311, filed on Oct. 9, 2004.

(30) Foreign Application Priority Data

Oct. 17, 2003 (DE) ................................. 103 48 283

(51) Int. Cl.
*G01N 21/00* (2006.01)
(52) U.S. Cl. .................... 422/56; 422/58; 422/82.05; 422/66
(58) Field of Classification Search ............ 422/56, 422/58, 82.05, 66
See application file for complete search history.

(56) References Cited

U.S. PATENT DOCUMENTS

| 5,228,972 | A | | 7/1993 | Osaka et al. |
| 5,525,297 | A | | 6/1996 | Dinger et al. |
| 5,609,823 | A | * | 3/1997 | Harttig et al. ................. 422/66 |
| 6,475,436 | B1 | | 11/2002 | Schabbach et al. |
| 7,378,270 | B2 | | 5/2008 | Azarnia et al. |
| 2002/0188224 | A1 | | 12/2002 | Roe et al. |

FOREIGN PATENT DOCUMENTS

| WO | WO 01/23885 A1 | 4/2001 |
| WO | WO 02/100274 A1 | 12/2002 |

* cited by examiner

*Primary Examiner*—Lore Jarrett
(74) *Attorney, Agent, or Firm*—Bose McKinney & Evans LLP

(57) ABSTRACT

The present invention provides a portable blood sugar measuring device comprising a tape unit for winding a test tape forward in sections, a detection unit for detecting measured values on the sections of tape to which body fluid has been applied, and a housing to hold the tape unit and detection unit. The tape unit and/or the detection unit can be deflected relative to the housing from an operating position against a flexible restoring element when subjected to a shock load. Also disclosed is a novel cover having open and closed positions. The cover is positioned at an opening of the housing through which the receiving site of the tape unit protrudes. The cover thus protects the receiving site from external effects when the cover is in the closed position. Similarly, the receiving site is accessible to apply body fluid thereto when the cover is in the open position.

18 Claims, 2 Drawing Sheets

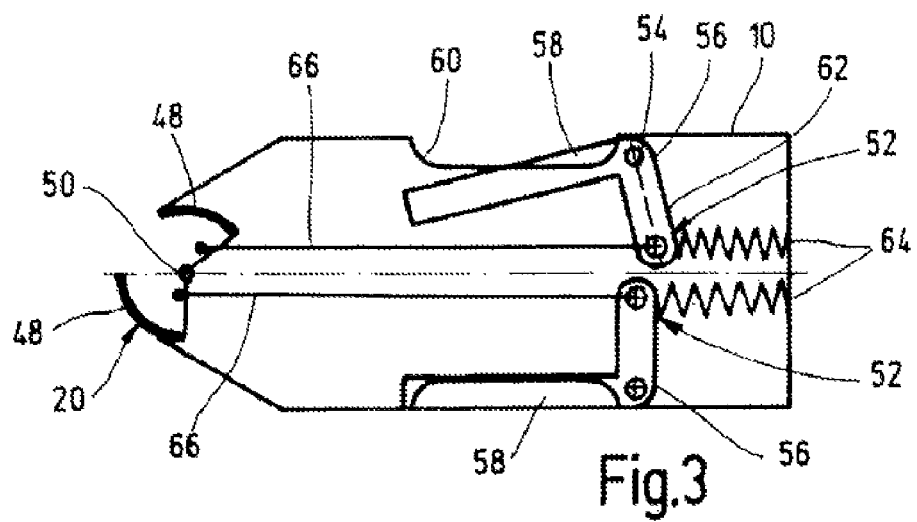
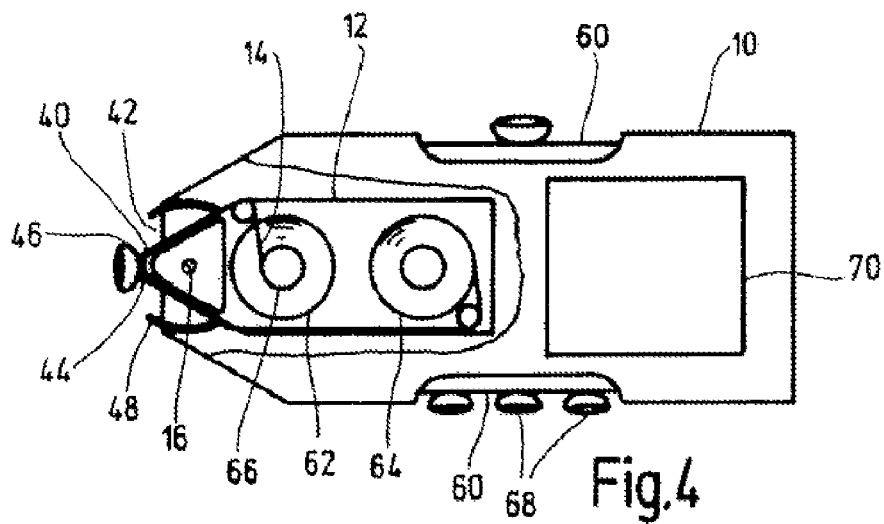
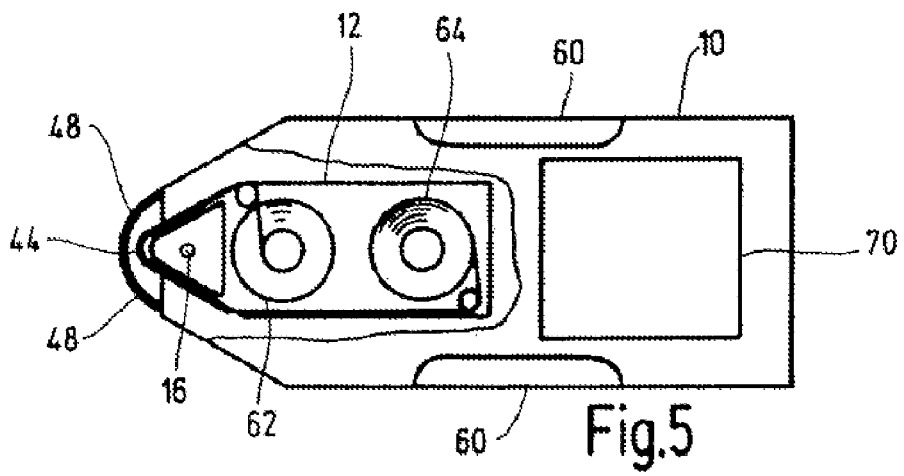

MANUAL DEVICE FOR EXAMINING A BODY FLUID

RELATED APPLICATIONS

This is a divisional application of U.S. application Ser. No. 11/405,257, filed Apr. 17, 2006, now U.S. Pat. No. 7,758,808, which is a continuation application of International Application PCT/EP2004/011311, filed Oct. 9, 2004, which claims priority to DE 103 48 283.0, filed on Oct. 17, 2003, all of which are incorporated herein by reference.

BACKGROUND

The present invention relates in general to a handheld test device for analyzing a body fluid and in particular to a portable blood sugar measuring device having a tape unit for advancing a test tape in sections, a detection unit for recording measured values on the test tape sections to which body fluid has been applied in the area of a receiving position, and a housing for holding the tape unit and detection unit.

Regular blood sugar monitoring is essential for diabetics because their treatment, diet and rhythm of life must often be adjusted based upon their monitored glucose levels. Handheld instruments that operate as "mini-laboratories" are widely available for self-monitoring and allow the necessary steps to be carried out simply and rapidly, even by laymen. Typically, disposable test strips are provided that are inserted into the instrument for determining glucose level, for example, by an optical measuring unit after the test strip is dosed with capillary blood. However, the storage and processing of these test strips require a large amount of space and also require complicated drives.

EP Applications No. 02026242.4 and 02028894.0 propose that a wound test tape on which a plurality of test sections provided with a suitable test chemistry are arranged consecutively should be used instead of individual test strips. The body fluid is applied and analyzed on a test section that is moved into an active position by advancing the tape. These patent applications give details about blood collection and also on the known test media and detection systems, especially for blood glucose, to which reference is herewith made and the content thereof is incorporated into this application.

In order to exactly dose the smallest possible amounts of blood, it has been proposed to expose the test tape over a deflection head external to the housing. A problem with this approach is protecting the complicated and sensitive measuring arrangement against external influences and to exactly align the detection optics.

SUMMARY OF THE INVENTION

The present invention addresses the disadvantages noted above and provides a robust device that that operates reliably.

In one form thereof, the present invention provides a handheld device for analyzing a body fluid. The device comprises a tape unit configured to wind a test tape forward, the tape unit having a receiving site adapted to receive body fluid. The device includes a detection unit configured to analyze sections of the tape to which body fluid has been applied. A housing is provided which holds the tape unit and the detection unit. A flexible restoring element is disposed in the housing, and at least one of the tape unit and the detection unit are moveable relative to the housing from an operating position against the force of the flexible restoring element when subjected to a shock load.

As a result of the shock absorption provided by the device of the present invention, the sensitive measuring arrangement is not excessively stressed when an external force is applied, but rather can withdraw or retract inside the housing so that the main load is absorbed by stable housing structures. Moreover, the restoring force can enable an exact centering in the operating position without the structures concerned having to be manufactured with extreme precision.

For particularly good protection it is advantageous that the tape unit and/or the detection unit can be deflected away from the receiving position into the housing. In certain exemplary embodiments, the detection unit is elastically supported against the housing by means of the restoring element.

With regard to the force introduction and positioning in the operating position, it is advantageous when the tape unit and the detection unit are held in a defined position relative to one another by means of at least one rigid stop, in particular, opposing engagement surfaces, under the restoring force of the restoring element.

In order to simplify the handling it is advantageous when the tape unit and the detection unit can be detached from a mutual stop position by a release mechanism acting on the restoring element. In this connection, the release mechanism is advantageously connected to a housing cover to further simplify tape unit replacement.

In order to limit freedom of movement when absorbing a shock, it is advantageous when the detection unit and/or the tape unit are mounted in a housing guide preferably with a large degree of play, i.e., play which is not due to manufacturing tolerances. An advantageous embodiment provides that the detection unit and/or the tape unit are guided by a sliding carriage in the housing in a linearly of substantially linearly movable manner. A further simplification results from the fact that the sliding carriage can be driven by a gear unit using an advancing drive for the test tape.

The restoring element is advantageously elastic and in certain embodiments is spring-elastic or rubber-elastic. In this connection, in certain embodiments, the restoring element is formed by a spring and in particular by a pressure spring pretensioned in the operating position.

In exemplary embodiments, the tape unit has a receiving head which protrudes from the housing in the operating position in order to expose the test tape outside the housing. In order to initially absorb the load from a shock, it is advantageous that the receiving head is formed from spring steel that is designed to be elastically deformable.

In another form thereof, the present invention provides a handheld device for analyzing a body fluid, comprising a tape unit configured to wind a test tape forward in sections and having a receiving site adapted to receive body fluid. A detection unit is provided that is configured to analyze sections of the tape to which body fluid has been applied. A housing is provided which holds the tape unit and the detection unit. A cover is attached to the housing, the cover having open and closed positions, whereby the receiving site can be screened from external effects when the cover is in the closed position and whereby the receiving site is accessible to apply body fluid thereto when the cover is in the open position.

Thus, the cover of the present invention enables sensitive instrument structures to be protected from external forces and also from penetration by contamination. This protection is effective in the resting state when the cover is closed.

In certain embodiments, the cover advantageously includes a closing member which can move relative to the housing and is preferably in the form of a flap, slide plate or roller blind. The cover closes an opening in the housing which bounds the receiving site.

In another exemplary embodiment, when the device is activated, the cover automatically moves into the open position. In this connection, it is advantageous when a tape drive that is activated when forwarding the test tape at the same time also moves the cover device into the open position.

In order to further improve the protective effect, it is advantageous when the cover can be moved into the open position when the device is operated manually and can be automatically moved into the closed position when the housing is released.

In order to simplify the handling and the closing function it is advantageous when the cover has a spring mechanism which is pretensioned in the open position preferably by actuating grip elements on the housing. It is also conceivable that a power supply inside the device is automatically switched on by a switch or switching element when the cover is opened.

In another aspect of the invention, the tape unit is advantageously formed by an exchangeable cassette whereas the sections of test tape are formed by reagent fields that respond to a constituent of the body fluid and are applied in sections to a continuous carrier tape.

BRIEF DESCRIPTION OF DRAWINGS

The above-mentioned aspects of the present invention and the manner of obtaining them will become more apparent and the invention itself will be better understood by reference to the following description of the embodiments of the invention taken in conjunction with the accompanying drawings, wherein:

FIG. 3 is a plan view illustrating another embodiment of a blood sugar measuring device having a closing device in an open and closed position in accordance with the present invention;

FIG. 4 is a plan view with portions broken away illustrating a blood sugar measuring device with an opened closing device for blood application to a test tape in accordance with the present invention; and FIG. 5 is a plan view with portions broken away illustrating the blood sugar measuring device of FIG. 4 with a closed closing device.

Corresponding reference characters indicate corresponding parts throughout the several views.

DETAILED DESCRIPTION

Figure 1:
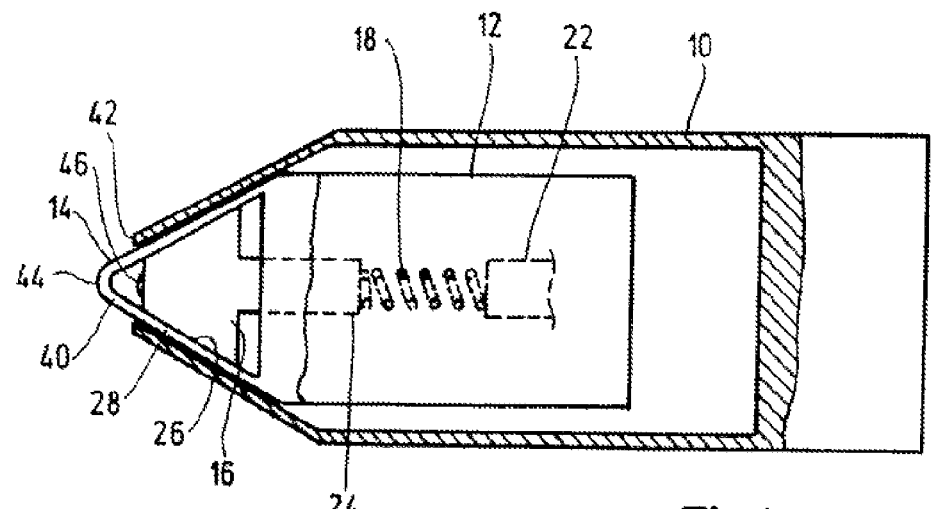
FIG. 1 is a plan view in partial cross section with portions broken away illustrating a shock-protected blood sugar measuring device for diabetics in accordance with an embodiment of the present invention.

The embodiments of the present invention described below are not intended to be exhaustive or to limit the invention to the precise forms disclosed in the following detailed description. Rather, the embodiments are chosen and described so that others skilled in the art may appreciate and understand the principals and practices of the present invention.

The blood sugar measuring device shown in the illustrated embodiments includes a housing 10 which can be held in the hand, a tape cassette 12 with the test tape 14 that is inserted into the housing, a detection unit 16 which operates optically for analysing blood applied to the test tape, and a spring-elastic restoring element 18 and/or a cover or closing device 20 for impact protection.

As shown in FIG. 1, the restoring element 18 is formed by a compression spring, which is pretensioned along the longitudinal axis of the device with its spring ends attached to a support 22 that is fixed in the housing and an arm 24 of the detection unit 16. The restoring force of the compression spring 18 has the effect that the detection unit 16 and the tape unit 12 are held in a defined stop position relative to one another and to the housing 10 by means of wedge-shaped stop faces 26, 28.

Figure 2:
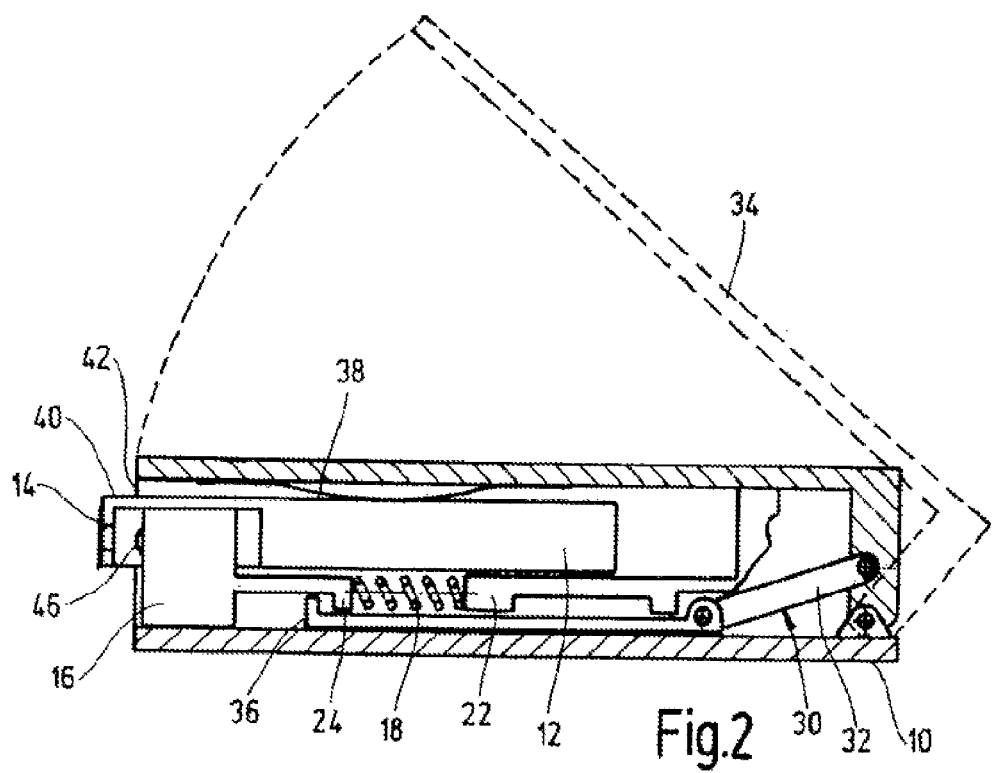
FIG. 2 shows the blood sugar measuring device of FIG. 1 in a longitudinal sectional view perpendicular to FIG. 1.

According to FIG. 2, the tape cassette 12 can be detached from its stop position by a release mechanism 30 in order to replace it. The release mechanism 30 has a connecting lever 32 which is pivoted at its ends on a housing flap 34 and on a draw hook 36. The draw hook 36 is pulled back when the housing flap 34 is swung open (dashed line in FIG. 2). At about half the return distance, the draw hook engages the arm 24 of the detection unit 16 and pulls it back against the force of the restoring spring such that the tape cassette 12 is released and can be removed. When the housing flap 34 is closed, a leaf spring 38 ensures that the tape cassette 12 rests on the detection unit 16 and in the housing 10 in a force-locking or secure manner.

In the stop position shown in FIGS. 1 and 2, the tape cassette 12 and the detection unit 16 are in an operating position for acquiring measured data. In this position, a conical receiving head 40 of the tape cassette 12 projects from a measuring opening 42 of the housing 10 and thus enables a dosed application of blood on the receiving site 44 in the area of its tip. The receiving head 40 forms a guide for the test tape 14 that is exposed to the outside, the test tape being wound in sections in the interior of the tape cassette by means of winding spools that are not shown in FIGS. 1 and 2.

The test tape 14 has a plurality of reagent fields that are applied spaced apart on a continuous transparent carrier tape and are brought successively into use by appropriately winding the tape and reacting the reagent fields to an analyte in a drop of blood applied thereto, which results in a color change. This reaction is detected by a reflection photometric measurement by means of the optical system 46 of the detection unit 16. In the operating position, the optics of system 46 are exactly focused on the receiving site 44.

In the case of shock loading (i.e., absorbing shock), for example, when the device is accidentally dropped, the receiving head 40, which is in contact with the sensitive detection unit 16, can withdraw or retract inside the housing against the restoring force of the compression spring 18, such that the load is essentially absorbed by the stable housing 10. There is sufficient free space between the detection unit 16 and the draw hook 36 (see FIG. 2) such that movement may take place along the path of the spring. Moreover, when the receiving head is positioned away from the stop position there is some freedom of movement relative to the housing in all axes of freedom so that an impact that is not directed axially can be absorbed in a favorable manner. The receiving head 40, for example, in the form of a spring steel guide, is expediently designed to be elastically deformable in order to absorb initial peak forces.

Although not specially illustrated in the Figs., the detection unit 16 and the tape cassette 12 can be guided on a slide carriage in the housing to allow a linear movement. The spool drive for the test tape, which is in any case required, can be used as the drive, the rotary movement being converted by a gear into a linear movement of the slide carriage.

In the embodiments shown in FIGS. 3 to 5, the area of the receiving site 44 is exposed when the closing device 20 is positioned in the open position as shown in FIG. 4. Blood application, for example, from a finger tip 46 (FIG. 4), can be screened from the action of external forces in the closed position (FIG. 5). For this purpose the closing device 20 has two half-shell flaps 48 which pivot around a common axis of rotation 52.

According to FIG. 3 each closing flap 48 can be actuated by means of its own spring mechanism 50. This mechanism comprises a two-armed hand lever 56, the driving arm 58 of which projects into a grip recess 60 of the housing 10, its angled support arm 62 being supported against the housing 10 via a spring 64 and connected to a closing flap 48 via a rod 66. The closing flap 48 is held in the closed position under spring tension as shown in FIG. 3 for the lower half of the housing. If the driving arm 58 is operated manually against the force of the spring 64, the rod 66 pulls the closing flap 48 into the open position shown at the top of FIG. 3. In this manner, it is possible for the closed position to be automatically adopted when the device is intentionally or accidentally released.

The embodiment shown in FIGS. 4 and 5 includes electrical grip switches 60 which in the spring-loaded pressed switch position activates the device and thus opens the closing flaps 48 by a motor drive. For this purpose it is possible to use a tape drive 66 which drives the winding spools 62, 64 of the tape cassette 12, which can be connected to the closing flaps 48 by a suitable gear means. In the activated state, the device is held by the fingers 68 in one hand while blood is collected as described above from a finger 46 of the other hand and analysed and the result of the measurement can be read by means of the display 70. When the device is put down and released the closing flaps 48 are automatically closed over the opening 42, thus screening the receiving site 44 from intruding contamination.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A handheld device for analyzing a body fluid, comprising:
    a tape unit configured to wind a test tape forward in sections and having a receiving site adapted to receive body fluid;
    a detection unit configured to analyze sections of the tape to which body fluid has been applied;
    a housing which holds the tape unit and the detection unit, the housing having an opening which provides access to the receiving site of the tape unit;
    a cover attached to the housing, the cover having open and closed positions and an elastic element biasing the cover in the closed position, the cover covering the opening in the closed position, wherein the receiving site can be screened from external effects when the cover is in the closed position and whereby the receiving site is accessible to apply body fluid thereto when the cover is in the open position; and
    a switch in communication with the cover and configured to automatically switch on a power supply inside the device when the cover is opened.

2. The handheld device of claim 1, wherein the cover has at least one closing member which can move relative to the housing.

3. The handheld device of claim 1, wherein the cover is configured to close an opening in the housing which bounds the receiving site.

4. The handheld device of claim 1, wherein the cover automatically moves into the open position when the device is activated.

5. The handheld device of claim 1, further comprising a tape drive that forwards the test tape and moves the cover into the open position.

6. The handheld device of claim 1, wherein the cover moves into the open position when the device is operated manually and automatically moves into the closed position when the housing is released by the user.

7. The handheld device of claim 1, wherein the tape unit comprises an exchangeable cassette.

8. The handheld device of claim 1, further comprising a flexible restoring element disposed in the housing, at least one of the tape unit and the detection unit being deflectable relative to the housing against the flexible restoring element when subjected to a shock load.

9. The handheld device of claim 8, wherein the flexible restoring element comprises a spring connected to the detection unit.

10. The handheld device of claim 8, wherein the at least one of the tape unit and the detection is movable along multiple axes of freedom when subjected to a shock load.

11. A handheld device for analyzing a body fluid, comprising:
    a tape unit configured to wind a test tape forward in sections and having a receiving site adapted to receive body fluid;
    a detection unit configured to analyze sections of the tape to which body fluid has been applied;
    a housing which holds the tape unit and the detection unit, the housing having an opening which provides access to and bounds the receiving site of the tape unit;
    a cover attached to the housing, the cover having open and closed positions, the cover covering the opening in the closed position, wherein the receiving site can be screened from external effects when the cover is in the closed position and whereby the receiving site is accessible to apply body fluid thereto when the cover is in the open position; and
    a grip element disposed on the housing and operatively connected to the cover, the grip element comprising a movable member having an elastic element connected thereto, wherein actuation of the grip element opens or closes the cover.

12. The handheld device of claim 11, wherein the movable member projects into the housing.

13. The handheld device of claim 12, wherein movement of the grip element against the force of the elastic element causes the cover to open.

14. The handheld device of claim 13, wherein the elastic element comprises a spring.

15. The handheld device of claim 11, further comprising a motor operatively connected to the cover, the grip element comprising an electrical grip switch in communication with the motor, wherein actuation of the grip element causes the motor to open or close the cover.

16. The handheld device of claim 15, wherein the motor is connected to and drives the tape unit.

17. The handheld device of claim 11, further comprising a flexible restoring element disposed in the housing, at least one of the tape unit and the detection unit being deflectable relative to the housing against the flexible restoring element when subjected to a shock load.

18. The handheld device of claim 17, wherein at least one of the tape unit and the detection is movable along multiple axes of freedom when subjected to a shock load.

* * * * *